(12) United States Patent
Schafer et al.

(10) Patent No.: US 7,972,831 B2
(45) Date of Patent: Jul. 5, 2011

(54) LIPASES FROM THERMOPHILIC ANAEROBES

(75) Inventors: Thomas Schafer, Farum (DK); Garabed Antranikian, Seevetal (DE); Maryna Royter, Hamburg (DE); Tine Hoff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 767 days.

(21) Appl. No.: 11/574,996

(22) PCT Filed: Oct. 5, 2005

(86) PCT No.: PCT/DK2005/000639
§ 371 (c)(1),
(2), (4) Date: Mar. 9, 2007

(87) PCT Pub. No.: WO2006/037334
PCT Pub. Date: Apr. 13, 2006

(65) Prior Publication Data
US 2009/0029410 A1    Jan. 29, 2009

Related U.S. Application Data

(60) Provisional application No. 60/618,112, filed on Oct. 13, 2004.

(30) Foreign Application Priority Data

Oct. 8, 2004  (DK) .............................. 2004 01545

(51) Int. Cl.
| | |
|---|---|
| *C12N 9/16* | (2006.01) |
| *C12N 9/18* | (2006.01) |
| *C12N 9/20* | (2006.01) |
| *C12Q 1/34* | (2006.01) |
| *C12Q 1/44* | (2006.01) |
| *C07H 21/04* | (2006.01) |

(52) U.S. Cl. .......... 435/196; 435/197; 435/198; 435/18; 435/19; 536/23.2

(58) Field of Classification Search ........................ None
See application file for complete search history.

(56) References Cited

U.S. PATENT DOCUMENTS
6,537,787 B1    3/2003  Breton

FOREIGN PATENT DOCUMENTS
CN        1500868        6/2004

OTHER PUBLICATIONS

EMBL/UniProt Accession No. Q8R921, Hydrolase of the alpha/beta superfamily, Jun. 1, 2002.*
Whisstock et al. Quaterly Reviews of Biophysics, 2003, "Prediction of protein function from protein sequence and structure", 36(3): 307-340.*
Bao et al., Genome Research , vol. 12, pp. 689-700 (2002).
EMBL: AEO13133, Accession No. AEO13133 (May 12, 2002).
Nolling et al., Journal of Bacteriology, vol. 183, No. 16, pp. 4823-4838 (2001).
EMBL: AE007861, Accession No. AE007861 (Jul. 31, 2001).
Rogalska et al., Chirality, vol. 5, pp. 24-30 (1993).
International Search Report from PCT/DK2005/000639, Parent PCT filed on Oct. 5, 2005.

* cited by examiner

*Primary Examiner* — Anand U Desai
*Assistant Examiner* — Iqbal H Chowdhury
(74) *Attorney, Agent, or Firm* — Kristin J. McNamara

(57) ABSTRACT

The inventors have identified polypeptides having lipase activity in anaerobic thermophilic bacteria. Accordingly, the invention provides a process for hydrolyzing an ester bond in a substrate, which comprises treating the substrate with a particular lipase (a polypeptide having lipase activity). The invention also provides a lipase for use in the process and a polynucleotide encoding the lipase.

5 Claims, No Drawings ial application no. PA 2004 01545 filed Oct. 8, 2004 and U.S. provisional application No. 60/618,112 filed Oct. 13, 2004 the contents of which are fully incorporated herein by reference.

FIELD OF THE INVENTION

The present invention relates to a process for hydrolyzing an ester bond in a substrate by treating it with a lipase. It also relates to a lipase for use in the process and to a polynucleotide encoding the lipase.

BACKGROUND OF THE INVENTION

The strains *Thermoanaerobacter thermohydrosulfuricus* DSM 7021, *Thermoanaerobacter brockii* subsp. *brockii* DSM 1457 and *Caldanaerobacter subterraneus* subsp. *tengcongensis* DSM 15242 are publicly available.

The full genome sequence of *Thermoanaerobacter tengcongensis* has been published (Bao et al., Genome Res. 12, 689-700, 2002 (GenBank AE008691)). SWALL:Q8R921 shows a sequence 258 of amino acids, described as "hydrolases of the alpha/beta super-family" (AAM25001.1).

SUMMARY OF THE INVENTION

The inventors have identified polypeptides having lipase activity in anaerobic thermophilic bacteria.

Accordingly, the invention provides a process for hydrolyzing an ester bond in a substrate, which comprises treating the substrate with a lipase (a polypeptide having lipase activity). The invention also provides a lipase for use in the process and a polynucleotide encoding the lipase.

The polypeptide may have the sequence SEQ ID NO: 2 or 4 or have a high degree of identity to one of these, or it may be derived from one of these by substitution, deletion, and/or insertion of one or more amino acids.

The polynucleotide may have the sequence SEQ ID NO: 1 or 3 or have a high degree of identity or may hybridize to one of these, or it may be part of the genome present in strain DSM 7021, DSM 1457, or DSM 15242 that can be amplified with the pair of primers LipCtTb-For LipCtTb-Rev (SEQ ID NO: 5-6) or with the pair LipTtg-for and LipTtg-rev (SEQ ID NO: 7-8).

DETAILED DESCRIPTION OF THE INVENTION

Genomic DNA Source

DNA sequences encoding lipases may be isolated from anaerobic thermophilic strains of *Caldanaerobacter, Thermoanaerobacter, Thermoanaerobium* or *Clostridium*. Thus, DNA sequences and polypeptides shown in the sequence listing were isolated from the organisms indicated below. As indicated, identical sequences were obtained from two organisms.

| Taxonomic classification | Basonym | Deposit number | DNA sequence | Polypeptide sequence |
|---|---|---|---|---|
| *Thermoanaerobacter thermohydrosulfuricus* | *Clostridium thermohydrosulfuricum* | DSM 7021 | SEQ ID NO: 1 | SEQ ID NO: 2 |
| *Thermoanaerobacter brockii* subsp. *brockii* | *Thermoanaerobium brockii* | DSM 1457 | SEQ ID NO: 1 | SEQ ID NO: 2 |
| *Caldanaerobacter subterraneus* subsp. *tengcongensis* | *Thermoanaerobacter tengcongensis* | DSM 15242 | SEQ ID NO: 3 | SEQ ID NO: 4 |

The strains are commercially available from DSMZ—Deutsche Sammlung von Mikro-organismen und Zellkulturen GmbH, Mascheroder Weg 1b, 38124 Braunschweig, GERMANY.

Sequence Identity

Polypeptides and polynucleotides of the invention may have an identity above 70%, above 80%, above 90% or above 95% to any of SEQ ID NO: 1-4. The alignment of two sequences and the calculation of amino acid or nucleotide identity may be done as described in U.S. Pat. No. 6,162,628.

Lipase Properties

The lipase is active on a wide range of esters, particularly water-insoluble substrates, including triacyl glycerols (triglycerides) and p-nitrophenyl palmitate. The lipase exhibits an unusual preference for 2-positional ester bonds in triglycerides.

The lipase is S-anantioselective, forming (S)-alcohols from racemic esters.

Industrial Use

The lipase can be used as an additive to detergents, e.g. as described in WO 2002062973.

The lipase can be used to produce diglycerides from triglyceride and glycerol.

The lipase can be used for enantioselective ester hydrolysis by hydrolysis of a racemic ester mixture. An example is (S)-(−)-3-butyn-2-ol which is useful as a pharmaceutical intermediate.

The lipase can be used in baking by adding it to a dough to prepare a dough-based product, particularly a baked product, e.g. as described in WO 9826057, WO 0032758, WO 2003100044, WO 2004064537 or Danish patent application PA 2003 01762.

The lipase can be used for transesterification of triglycerides, e.g. as described in WO 9522606 or WO 9933964.

The lipase can be used ester synthesis for example in biodiesel production.

The lipase can be used for polymerization reactions for example condensation of diacids and dialcohols.

EXAMPLES

Example 1

Amplification of the Complete Lipase Gene

The complete lipase genes from *Thermoanaerobacter thermohydrosulfuricus* DSM7021 and *Thermoanaerobacter brockii* subsp. *brockii* DSM 1457 were amplified with the following primers as indicated:

| Name | SEQ ID | Sequence | Length | Tm | % GC |
|---|---|---|---|---|---|
| LipCtTb-For | SEQ ID NO: 5 | 5'-ATGCAAAAGGCTG TTGAAATTAC-3' | 23 | 55.3° C. | 34.8% |
| LipCtTb-Rev | SEQ ID NO: 6 | 5'-TTATCCCTTTAAC AATTCCTTTTG-3' | 25 | 54.8° C. | 28.0% |

The complete lipase gene from *Caldanaerobacter subterraneus* subsp. *tengcongensis* DSM 15242 was amplified with the following primers as indicated:

| Name | SEQ ID | Sequence | Length | Tm | % GC |
|---|---|---|---|---|---|
| LipTtg-for | SEQ ID NO: 7 | 5'-ATGCAGAAGGC TGTAGAGTTTAC-3' | 23 | 58.9° C. | 43.5% |
| LipTtg-rev | SEQ ID NO: 8 | 5'-TTATCCCTTTAA TTCTCTTTCAAAG-3' | 25 | 54.8° C. | 28.0% |

Example 2

Production of Lipase from *T. thermohydrosulfuricus*

The strain DSM 7021 was cultivated on a rotary shaker (160 rpm) for 32 h at 65° C. in 50 ml bottles containing 20 ml of the corresponding liquid medium.

The basal medium contained (per liter): NaCl, 3.0 g; $KH_2PO_4$, 2.5 g; $NaH_2PO_4$, 0.8 g; $MgSO_4 \times 7H_2O$, 0.1 g; $CaCl_2 \times 2H_2O$, 0.05; $FeCl_3 \times 6H_2O$, 0.01 g; $(NH_4)_2SO_4$, 1.5 g; $SrCl_2 \times 6H_2O$, 0.03 g; $H_3BO_3$, 0.03 g; $Na_2WO_4$, 0.03 g; yeast extract, 1.5 g; peptone, 1.5 g; trace element solution 141, 1 ml, vitamin solution 141, 1 ml; resazurin, 0.001 g; $NaHCO_3$, 1.0 g; cysteine, 0.3 g; pH 7.2. Just prior to inoculation, 1 mg $Na_2S \times 9H_2O$ was injected in 20 ml containing bottles. Additionally, 0.05 g $Na_2S_2O_3$ was added to the bottles with medium.

The strain was grown on the complex medium described above and was found to synthesize extracellular lipase without lipase inductors in the medium containing 0.5% glucose as carbon and energy source. The production of the enzyme paralleled growth and reached its maximum (12 U/l) after 32 h of growth at temperature 65° C. and pH 7.2. About 89% of the enzyme was found to be secreted into the culture fluid. In presence of typical lipase inductors as olive oil and Tween 80 the lipase activity did not increase.

The organism was identified as a lipase producer with p-nitrophenyl palmitate and additionally with olive oil as substrates.

Example 3

Purification of Lipase from *T. thermohydrosulfuricus*

The extracellular lipase in the culture broth of Example 1 was purified by a three-step procedure. The first step was hydrophobic interaction chromatography. The lipase did not desorb within 1-0 M KCl gradient from Phenyl-Sepharose column, but eluted at 10-12% dimethylsulfoxide, separating well from the bulk of other proteins.

The lipase solution obtained after hydrophobic interaction chromatography was loaded on a hydroxilapatite column used as a second purification step. The lipase was eluted at the approximate mid-point of the sodium phosphate buffer gradient (220 to 250 mM range). The active fractions were further subjected to gel filtration column. The final gel filtration resulted in the three peaks. The enzyme activity was present in the second major peak. The lipase was purified approximately 133.5-fold over the crude extract with a 10.2% yield. The specific activity of the purified lipase was 12.3 U/mg.

SDS-PAG-electrophoresis of purified lipase heat-pretreated under the usual reducing conditions resulted in one protein band of a relative molecular mass of about 34.2 kDa. In the absence of detergent, the lipase migrated under native conditions by native PAG-electrophoresis and displayed a single band at 69 kDa, which was identical to the molecular mass of 68.5 kDa determined by gel filtration.

The activity of the band after native PAG-electrophoresis were determined, and activities with α-naphtyl acetate coincided with the Coomassie brilliant blue R-250 stained protein band. The lipolytic activity of the purified lipase after SDS-PAG-electrophoresis could be restored by removing the SDS with Triton X-100. This demonstrated, that the enzyme is also active a monomer. Any lipase activity was detected without treatment of Triton X-100 to wash.

Example 4

Cloning of Lipases from *C. thermohydrosulfuricum*, *T. brockii* and *T. tencongensis*

Strains, Plasmids and Media

Bacterial cloning experiments were carried out with either *E. coli* TOP-10 (Invitrogen) or Tuner™(DE3)pLacI (Novagen) using standard techniques. *E. coli* TOP-10 was used in combination with cloning vector pCR 2.1-TOPO (Invitrogen) suitable for blue/white assays. *E. coli* Tuner™ (DE3)pLacI was used in combination with vector pETBlue-1 (Novagen) containing the T7 promoter to clone and express the lipase gene. Lura-Betani medium was used for *E. coli* cells. Antibiotics were added at the followings concentrations: carbenicillin, 50 µg/ml; tetracycline, 15 µg/ml; chloramphenicol, 34 µg/ml; kanamycin, 50 µg/ml.

N-Terminal Amino Acid Sequence Analysis

The N-terminal amino acid sequence of the lipase from *C. thermohydrosulfuricum* and *T. brockii* were determined up to 17 amino acid residues. The N-terminal amino acid sequences are shown as residues 1-17 of SEQ ID NO: 2 and are 100% identical. Comparison of N-terminal sequences of the lipases from *Clostridium thermohydrosulfuricum* and *Thermoanaerobacter brockii* subsp. *brockii* with N-terminal sequence of the hydrolase (AAM2500 1.1) from *Thermoanaerobacter tencongensis* (strain MB4T, Genbank accession no. AE008691) shows a 88% homology.

Database Searching and Computational Analysis

Lipase gene sequences were obtained using the Entrez search and retrieval system at the National Center for Biotechnology Information (NCBI). Regions with homology to the lipase gene sequences were obtained using BLASTP at NCBI. Alignment of the lipase genes with the *Termoanaerobacter tencongensis* hydrolase gene was performed using CLUSTALW at eBioinformatics.

Example 5

PCR Amplification of the Lipase from *T. thermohydrosulfuricus* and *T. brockii* and Cloning in pCR 2.1-TOPO Vector PCR Amplification of the Lipase Gene Fragments DNA was extracted from bacterial strains *T. thermohydrosulfuricus* and *T. brockii* using QIAGEN Genomic DNA Kit for isolation of genomic DNA from bacteria. Chromosomal DNA was used as a template for amplification of lipase fragments using primers (Table 1) in all possible combinations. PCR reactions were performed according to the following conditions using a Biometra® thermal cycler (model T 3000 Thermocycler): template DNA was added to a final concentration of 1.5 ng $\mu l^{-1}$ in a buffer composed of 1×PCR-buffer, 3 mM $MgCl_2$, 0.2 mM dNTPs, and 0.15 U $\mu l^{-1}$ Taq-polymerase. Forward and reverse primers were added at a final concentration of 3 pmol $\mu l^{-1}$. Twenty five thermocycles were performed as follows: Seq1 (94° C., 20 s), Seq2 (55° C., 40 s), Seq3 (72° C., 1 min).

Oligonucleotides Used for PCR-Screening:

| SEQ ID | Name | Sequence | Function |
|---|---|---|---|
| NO: 9 | LF/NT/CTT | CTTAAGGGGATGTTGCATCTTC | Forward |
| NO: 10 | LF/NT/ATT | ATTAAGGGGGTACTGCATCTG | Forward |
| NO: 11 | LF/OAH/CAT | CATGGGTTTACCGGAAATAAAGTGG | Forward |
| NO: 12 | F/CRI/TTC | TTCAGGCGAAAGCGACGGAG | Forward |
| NO: 13 | F/CRI/GGA | GGAACAGGTGAAAGTGATGGAGAATT | Forward |
| NO: 14 | F/CRI/GCG | GCGGTGAAAGTGATGGAGACTTT | Forward |
| NO: 15 | R/CRI/TCC | TCCGTCGCTTTCGCCTGAAC | Reverse |
| NO: 16 | R/CRI/AAA | AAATTCTCCATCACTTTCACCTGTTCC | Reverse |
| NO: 17 | R/CRI/TCT | TCTCCATCACTTTCACCGCTG | Reverse |
| NO: 18 | R/CRII/CAA | TCCTCCCATGCTGAGTCCCAA | Reverse |
| NO: 19 | R/CRII/AAG | TCCTCCCATGCTGAAGCCAAG | Reverse |
| NO: 20 | R/CTI/TTT | TTTTGTATGGTCCGCTCCTTCTAT | Reverse |

Cloning of Lipase Gene Fragments

The selected PCR-amplificates were ligated into vector pCR2.1-TOPO and trans-formed in competent TOP-10 *E. coli* cells using standard cloning techniques (TA Cloning Kit, Invitrogen). Selection of positive clones follows by traditional blue/white screening. Plasmids were isolated using NucleoSpin Plasmid Kit (Macherey-Nagel).

PCR-Screening for Identification of Sequences with Homology to Lipases

The sequences were analyzed using BLASTN at NCBI. The 142-bp fragment with 84% identity to the nucleotide sequence of the hydrolase α/β superfamily from *Thermoanaerobacter tencongensis* was amplified with the primers F/CRI/GCG and R/CRII/CAA (SEQ ID NO: 14 and 18) using gDNA from *C. thermohydrosulfuricum* as template:

(SEQ ID NO: 21)
TGCGGTGAAAGTGATGGAGACTTTAGTGAAATGACATTTAGCAGTGAATT

GGAAGATGCAAGACAAATTTTAAAGTTTGTGAAAGAGCAACCTACGACTG

ACCCTGAGAGAATAGGACTACTTGGGACTCAGCATGGGAGGA

The 141-bp fragment with 81% identity to the nucleotide sequence of the hydrolase α/β superfamily from *Thermoanaerobacter tencongensis* was amplified with the primers F/CRI/GCG and R/CRII/AAG (SEQ ID NO: 14 and 19) using gDNA from *T. brockii* as template:

(SEQ ID NO: 22)
TGCGGTGAAAGTGATGGAGACTTTAGTGAAATGACATTTAGCAGTGAATT

GGAAGATGCAAGACAAATTTTAAAGTTTGTGAAAGAGCAACCTACGACTG

ACCCTGAGAGAATAGGACTACTTGGCTTCAGCATGGGAGGA

Example 6

Inverse PCR

Inverse PCR was conducted with DNA from *T. thermohydrosulfuricus* and *T. brockii* sp. *brockii*.

Digestion of gDNA with Restrictions Enzymes

Inverse PCR technique which allows the amplification of DNA segments that are outside of known sequence boundaries was used to complete the lipase gene. The genomic DNA (~1.4 µg) was digested into small fragments with restriction enzymes BamHI and HindIII 20 U each per reaction in 1×RE-buffer B. The digestion reaction was performed in 300 µl total volume for 24 h at 37° C. The restriction reaction was precipitated with ¹/₁₀ volume 3M NaOAc and 2.5 volume absolute ethanol for 2 h at −20° C., spin down for 30 min, at 13000 rpm, at 4° C. The pellet was air dried for 20 min at room temperature and than resuspend in 100 µl $ddH_2O$.

Self Ligation of the DNA-Fragments 0.5 µl (200 U) T4Ligase (MBI, BioLabs), 30 µl T4 Ligase-buffer (MBI) and 10 mM ATP were added to the digested DNA. The ligation reaction was carried out at 4° C. for 48 h. The ligation reaction was precipitated with ¹/₁₀ volume 3M NaOAc and 2.5 volume absolute ethanol for 2 h at −20° C., spin down for 30 min, at 13000 rpm, at 4° C. The pellet was air dried for 20 min at room temperature and than resuspend in 100 µl $ddH_2O$.

Inverse PCR with Constructed Primers

The circular DNA-fragments were used as templates for amplification of lipase fragments using primers (Table 2) in all possible combinations. PCR reactions were performed according to the following conditions using a Biometra® thermal cycler (model T 3000 Thermocycler): template circular DNA-fragments were added to a final concentration of ~1.35 ng $\mu l^{-1}$ in a buffer composed of 1×PCR-buffer, 3 mM $MgCl_2$, 0.2 mM dNTPs, and 0.15 U $\mu l^{-1}$ Taq-polymerase. Forward and reverse primers were added at a final concentration of 3 pmol $\mu l^{-1}$. Thirty thermocycles were performed as follows: Seq1 (94° C., 20 s), Seq2 (55° C., 45 s), Seq3 (72° C., 2 min).

TABLE 2

Oligonucleotides used for inverse PCR
I corrected the last columns of the table.

| SEQ ID | Name | Sequence | Length | Tm | % GC |
|---|---|---|---|---|---|
| 23 | 1F_Inv2CT | GACATTTAGCAGTGAATTGGAAGATGC | 27 | 62° C. | 41% |
| 24 | 2F_Inv2CT | TTTGTGAAAGAGCCTACGACTGACC | 25 | 63° C. | 48% |
| 25 | 3R_Inv2CT | GCACTTTACCCTTAACATCATCAGGC | 26 | 63° C. | 46% |
| 26 | 4R_Inv2CT | GACTCTACTTTATTGCCTGTAAAACCG | 27 | 62° C. | 41% |

The program ContigExpress™ (Vector NTI®, software package for Mac OS users developed by InforMax, Inc., North Bethesda, Md.) was used for analysis of the sequences and to complete the lipase gene.

Example 7

Expression of Lipases from *C. thermohydrosulfuricum*, *T. brockii* and *T. tencongensis*

AccepTor Vector Kit (Novagen) was used for IPTG-inducible expression of lipase genes under the control of the T7lac promoter in pETBlue-1 vector. The Kit is designed for simplified cloning of PCR products generated using Taq DNA polymerase, that leave single 3'-dA overhangs on their reaction products. The linearized pETBlue-1 vector contains single 3'-dU overhangs that are compatible with direct ligation of these products without the need for intermediate reactions. Following transformation, the dU residues are replaced with dT residues as the bacteria replicate the plasmid.

The NovaBlue host is used for initial cloning and verification of constructs in the pET-Blue-1 vector, and then the recombinant plasmids are transformed into the Tuner(DE3) pLacI strain for expression in *E. coli*.

Preparation of the Insert

Lipase genes were amplified by PCR. Chromosomal DNA was used as a template for amplification of complete lipase gene using constructed primers (SEQ ID NO: 5-6 for the lipase gene from *C. thermohydrosulfuricum* and *T. brockii*; SEQ ID NO: 7-8 for the lipase gene from *T. tencongensis*) as described above in Example 1. PCR reactions were performed according to the following conditions: template DNA was added to a final concentration of ~1.5 ng μl$^{-1}$ in a buffer composed of 1×PCR-buffer, 3 mM MgCl$_2$, 0.2 mM dNTPs. 0.2 U μl$^{-1}$ Hifi-polymerase was added after hot-start. Forward and reverse primers were added at a final concentration of 3 pmol μl$^{-1}$. Twenty five thermocycles were performed as follows: Seq1 (94° C., 15 s), Seq2 (50° C., 30 s), Seq3 (68° C., 1 min 20 s). PCR-products were purified using NucleoSpin Extraction Kit (Macherey Nagel).

Ligation 50 ng μl$^{-1}$ pETBlue-1 vector were ligated with ~50 ng amplified product in a total volume of 10 μl. The reaction was incubated at 16° C. for 1 h.

Transformation of NovaBlue Singles™ Competent Cells

For transformation, 1 μl of the ligation reaction was added directly to NovaBlue Singles Competent Cells. The transformation was performed by "heat shock" method for exactly 30 sec in a 42° C. water bath. The positive clones were selected for the carbenicillin resistance marker by blue/white screening.

Transformation of Tuner™(DE3) pLacI Competent Cells with pETBlue-1 Recombinants pETBlue-1 recombinants identified and isolated from the blue/white screening host NovaBlue were transformed into Tuner(DE3)pLacI expression host for IPTG-based induction. This strain carries a chromosomal copy of the T7 RNA polymerase gene and is designed for IPTG-inducible expression of target genes under the control of the T7lac promoter in pETBlue-1 vector. ~1 ng μl$^{-1}$ of the pETBlue-1 recombinant plasmid was added directly to the competent cells. The transformation was performed by "heat shock" method for 30 sec in a 42° C. water bath.

Growth and Induction 3 ml of starter culture of the pETBlue-1 recombinant in a (DE3)pLacI expression host strain were prepared. The growth LB medium contains carbenicillin, 50 μg ml$^{-1}$; chloramphenicol, 34 μg ml$^{-1}$ and 1% glucose. 100 ml medium inoculated with starter culture was incubated to an OD$_{600}$ of 1.0. Than 1 mM IPTG was added. The culture was incubated with shaking at 37° C. for 4 h for full induction.

Example 8

Expression of *T. thermohydrosulfuricus* Lipase in *Bacillus subtilis*

A linear integration vector-system was used for the expression cloning of the gene. The linear integration construct was a PCR fusion product made by fusion of the gene between two *Bacillus subtilis* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003095658). The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as marker. (Described in eg. Diderichsen, B.; Poulsen, G. B.; Joergensen, S. T.; A useful cloning vector for *Bacillus subtilis*. Plasmid 30:312 (1993)). The final gene construct was integrated on the *Bacillus* chromosome by homologous recombination into the pectate lyase locus.

Chromosomal DNA of *T. thermohydrosulfuricus* was isolated by QIAmp Tissue Kit (Qiagen, Hilden, Germany). First 3 fragments were PCR amplified: the gene fragment with specific primers oth296 (SEQ ID NO.: 27) and oth297 (SEQ ID NO.: 28) on genomic DNA from *T. thermohydrosulfuricus*. The upstream flanking fragment was amplified with the primers 260558 (SEQ ID NO.: 29) and iMB1361Uni1 (SEQ ID NO.: 30) and the downstream flanking fragment was amplified with the primers 260559 (SEQ ID NO.: 31) and DwC 1361 (SEQ ID NO.: 32) from genomic DNA of the strain iMB1361 (described in patent application WO 2003095658.

The gene fragment was amplified using a proofreading polymerase (Proof Start Polymerase (Qiagen)). The two flanking DNA fragments was amplified with "Expand High Fidelity PCR System" (Boehringer Mannheim, Germany). The PCR reactions were made according to standard procedures (following the manufacturer's recommendations). The PCR conditions were as follows: 94° C. for 2 min followed by 10 cycles of (94° C. for 15 sec, 50° C. for 45 sec, 68° C. for 4 min) followed by 20 cycles of (94° C. for 15 sec, 50° C. for 45 sec, 68° C. for 4 min (+20 sec. extension pr cycle)) and ending with one cycle at 68° C. for 10 min.

The 3 resulting fragments were mixed in equal molar ratios and a new PCR reaction were run under the following conditions: initial 2 min. at 94° C., followed by 10 cycles of (94° C. for 15 sec., 50° C. for 45 sec., 68° C. for 5 min.), 10 cycles of (94° C. for 15 sec., 50° C. for 45 sec., 68° C. for 8 min.), 15 cycles of (94° C. for 15 sec., 50° C. for 45 sec., 68° C. for 8 min. in addition 20 sec. extra pr cycle). After the 1$^{st}$ cycle the two end primers 260558 (SEQ ID NO.: 29) and 260559 (SEQ ID NO.: 31) was added (20 pMol of each). Two μl of the PCR product was trans-formed into *Bacillus subtilis* and transformants was selected on LB-plates containing chloramphenicol (6 μg/ml medium). A clone containing the construct without mutations leading to amino acid changes was selected for fermentation in liquid media.

Fermentation, Purification and Activity Assay

The clone was streaked on an LB-agar plate with 6 micro g/ml chloramphenicol from −80° C. stock, and grown overnight at 37° C. The colonies were transferred to 100 ml LB or PS-1 media supplemented with 6 micro g/ml chloramphenicol in a 500 ml shaking flask. The culture was shaken at 30° C. at 275 rpm for 1 or 3 days. The cells were spun down and the enzyme purified from the supernatant by already described methods in example 3. The activity was measured as already described in example 9.

Example 9

Properties of Lipase

Effect of Temperature

Purified lipases of SEQ ID NO: 2 and 4 both showed optimum activity 75° C. (10 minutes reaction) with little activity above 85-90° C.

Effect of pH

Purified lipase of SEQ ID NO: 2 showed optimum activity at pH 8.0, >80% activity at pH 6.5-9.0, and almost no activity below pH 6.0 and above pH 10.0. The lipase of SE ID NO: 4 showed optimum activity at pH 7.0, >60% activity at pH 6.5-9.0, and almost no activity below pH 6.0 and above pH 11.0.

Effects of Metal Ions

The lipase activity was nearly unchanged in the presence of the following metal ions up to 10 mM: Na+, K+, Ca2+, Cu2+, Ag+ Mg2+, Mn2+, Sr2+, Rb+, Co2+, Ni2+ and Al3+. The activity was decreased by the following ions: Zn2+, Fe2+, Fe3+ and Cr3+.

Effect of Detergent Ingredients

The activity of the lipase was tested after incubation for 1.5 hours at 30° C. with up to 10% by weight of various compounds. The lipase maintained >75% activity after incubation with CHAPS (3-[(3-cholamidopropyl)dimethylammonio]-1-propanesulfonic acid), PVA (polyvinyl alcohol) and EDTA (ethylenediamine tetra-acetic acid). Incubation with Tween-20 and Tween-80 or Triton X-100 decreased the activity. SDS caused full enzyme inhibition.

Effect of Solvents

The following solvents at concentrations up to 50% by volume had little effect on the activity of the lipase of SEQ ID NO: 2: tert-butanol, ethanol, acetonitrile, isopropanol, pyridine, DMSO, acetone, dimethylformamide and methanol.

Effect of Inhibitors

The following compounds had little effect on the activity of the lipases of SEQ ID NO: 2 and 4 at concentrations up to 10 mM: b-mercaptoethanol, urea, pHMB, guanidine hydrochloride, DTT and iodo-acetate. Both lipases were inactivated by PMSF and Pefablock at 0.1-1 mM.

Example 10

Substrate Specificity of Lipase from *T. thermohydrosulfuricus*

Substrate Specificity for pNP-Esters

The lipase of SEQ ID NO: 2 was tested by reaction with various pNP-esters 1 mM (pH 8.0) as substrates for 10 min at 70° C. Similar results were obtained with the lipase of SEQ ID NO: 4.

| pNP-esters | Relative activity |
| --- | --- |
| pNP-acetate (C2:0) | 9 |
| pNP-butyrate (C4:0) | 57 |
| pNP-caproate (C6:0) | 81 |
| pNP-caprylate (C8:0) | 90 |
| pNP-caprate (C10:0) | 100 |
| pNP-laurate (C12:0) | 84 |
| pNP-myristate (C14:0) | 68 |
| pNP-palmitate (C16:0) | 32 |
| pNP-stearate (C18:0) | 8 |

It is seen that the lipase has high activity with substrates of chain length C6-C14.

Substrate Specificity with Triacylglycerols

The lipase of SEQ ID NO: 2 was tested by reaction with various triacylglycerols 10 mM (pH 8.0) as substrates: for 25 h at 70° C. Similar results were obtained with the lipase of SEQ ID NO: 4.

| Triacylglycerols | Relative activity |
| --- | --- |
| Triacetin (C2:0) | 5 |
| Tributyrin (C4:0) | 10 |
| Tricaproin (C6:0) | 74 |
| Tricaprylin (C8:0) | 100 |
| Tricaprin (C10:0) | 15 |
| Trilaurin (C12:0) | 11 |
| Trimyristin (C14:0) | 8 |
| Tripalmitin (C16:0) | 22 |
| Tristearin (C18:0) | 9 |
| Triolein (C18:1) | 12 |
| Olive oil | 10 |

It is seen that the lipase has good activity with C6 and C8, but low activity with other chain lengths.

Example 11

Alcoholysis

Alcoholysis of various triacylglycerols catalyzed by the lipase of SEQ ID NO: 2 were tested. All substrates were alcoholyzed by the lipase. The highest yield was observed with tristearin as substrate (conversion 67%). For other substrates the conversions were above 40%. The lipase catalysed the synthesis of 1,3-diacylglycerides and 1- and 3-monoacylglycerides from triacylglycerides at highest rate. No sn2-monoglyceride was produced. The enzyme exhibited unusual preference to 2-positional ester bonds. With the length of the ester bonds the 2-positional specificity of the protein increased.

Example 12

Enantioselectivity

The lipase of SEQ ID NO: 2 was found to be active towards the following four substrates: 1-phenyl-1-ethyl-acetate, 1-phenyl-2-propyl-acetate, butynol acetate and butynol butyrate, and relative S-anantioselective towards the two latter. With these two substrates the lipase showed (S)-preference and acceptable E-values (16.7 and 9.2 accordantly). The (S)-alcohols were formed. The lipase was more enantioselective towards butynol butyrate than towards butynol acetate. Over time the conversion increased for all four substrates and reached above 20-30% after 24 h of reactions time. Over time in the contrast to the conversion the enantioselectivity of the enzyme towards both substrates decreased for butynol butyrate from 16.7 to 8.06 and for butynol acetate from 9.15 to 2.65 after 40 h of reactions time. The lipase showed higher preference for (S)-enantiomers, but over time its ability to distinguish between enantiomers decreased. For two other substrates the enantioselectivity of the lipase (E≧1) was constant over time.

Example 13

Positional Specificity

Positional Specificity Towards Monoglycerides (MG)

The hydrolysis of the 1-positional ester bond with the lipase of SEQ ID NO: 2 was found to be lower (less than 2 fold) in comparison with 2-positional ester bond in monopalmitoyl glycerols molecule. The enzyme exhibited unusual preference to 2-positional ester bonds.

Positional Specificity Towards Triglycerides (TG)

The positional specificity of the lipase from *T. thermohydrosulfuricum* (SEQ ID NO: 2) was tested towards the following triglycerides (TG, triacylglycerols): trilaurin (C12), trimyristin (C14), tripalmitin (C16), tristearin (C18), Triolein (C18:1). Each TG (3 mmol) was dissolved in organic solvent (2 ml acetone) and pre-equilibrated at 65° C. for 15 min, 400 rpm. Dry ethanol (3 mmol) was added and reaction mixture was incubated at 65° C. for 15 min, 400 rpm. Lipase (10% based on TG weight) was added to start reaction. Reaction was carried out in a 4-ml screw-capped vial and the reaction mixture was mixed with magnetic stirrer (400 rpm). Aliquot amount of reaction mixture (20 µl) was periodically withdrawn and diluted with chloroform (80 µl) to appropriate dilution, followed by analysis with latroscan to determine acylglycerol composition.

Changes in glycerides composition of the reaction medium during reaction were quantitatively determined by TLC/FID using latroscan analytical methods (latroscan, latron Laboratories, Inc., Tokyo, Japan). Before analysis, a blank of the chromarod was scanned. After treating chromarod with boric acid (3%) and drying for 5 min, 0.1 µl of the reaction medium (diluted in chloroform at appropriate dilution) is spotted onto the chromarod and the spotted sample was developed for 10 cm in a mixture of benzene:chloroform:acetic acid (50:30:0.5, by vol) for 35 min. After drying, the chromarod in an oven at 110° C. for 5 min, scanning is performed at a hydrogen flow rate of 160 ml/min and an air flow rate of 2.0 l/min to produce a chromatogram.

The results of the alcoholysis of the triacylglycerols catalysed by the lipase from *C. thermohydrosulfuricum* after 7 h reactions time at 65° C. are given below as % of remaining substrate (TG) and % of the following products: fatty acid (FA), diglycerides (DG, with 1,3-DG separated from 1,2- and 2,3-DG), monoglyceride (MG, with 2-MG separated from 1- and 3-MG).

|  | TG | FA | DG 1,3- | DG 1,2- 2,3- | MG 2- | MG 1- 3- |
|---|---|---|---|---|---|---|
| Trilaurin (C 12) | 58 | 2 | 12 | 6 | — | 22 |
| Trimyristin (C 14) | 66 | 1 | 12 | 2 | — | 19 |
| Tripalmitin (C16) | 65 | 3 | 13 | 1 | — | 18 |
| Tristearin (C 18) | 33 | 10 | 48 | — | — | 9 |
| Triolein (C18:1) | 63 | 2 | 18 | — | — | 17 |

The results show that all substrates were alcoholyzed by the lipase. The highest yield was observed with tristearin as substrate (conversion 67%). For other substrates the conversions were above 40%. The lipase catalysed the formation of the 1,3-diacylglycerides and 1- and 3-monoacylglycerides from triacylglycerides at highest rate. No sn2-monoglyceride was produced. The enzyme exhibited unusual preference to 2-positional ester bonds. With the length of the ester bonds the 2-positional specificity of the protein increased.

The invention claimed is:

1. An isolated polypeptide having lipase activity, and having at least 90% identity to the polypeptide of SEQ ID NO: 2.

2. The polypeptide of claim 1, which has at least 95% identity with SEQ ID NO: 2.

3. A process for hydrolyzing an ester bond in a substrate, which comprises treating the substrate with the polypeptide of claim 1.

4. The process of claim 3, wherein the ester bond is a secondary alcohol ester bond.

5. The process of claim 4, wherein the ester bond is a bond in the 2-position of a triglyceride.

* * * * *

SEQUENCE LISTING

<160> NUMBER OF SEQ ID NOS: 32

<210> SEQ ID NO 1
<211> LENGTH: 780
<212> TYPE: DNA
<213> ORGANISM: Thermoanaerobacter thermohydrosulfuricus
<220> FEATURE:
<221> NAME/KEY: CDS
<222> LOCATION: (1)..(777)

<400> SEQUENCE: 1

```
atg caa aag gct gtt gaa att aca tat aac ggc aaa act tta aga gga      48
Met Gln Lys Ala Val Glu Ile Thr Tyr Asn Gly Lys Thr Leu Arg Gly
1               5                   10                  15
```

```
atg atg cat ttg cct gat gat gtt aag ggt aaa gtt cct atg gta ata      96
Met Met His Leu Pro Asp Asp Val Lys Gly Lys Val Pro Met Val Ile
         20                  25                  30 atg ttt cac ggt ttt aca ggc aat aaa gta gag tct cac ttt att ttt     144
Met Phe His Gly Phe Thr Gly Asn Lys Val Glu Ser His Phe Ile Phe
         35                  40                  45 gtg aag atg tca aga gct tta gaa aaa gta ggt att ggg agt gta agg     192
Val Lys Met Ser Arg Ala Leu Glu Lys Val Gly Ile Gly Ser Val Arg
     50                  55                  60 ttt gac ttt tat ggt tct gga gaa agt gat ggg gac ttt agt gaa atg     240
Phe Asp Phe Tyr Gly Ser Gly Glu Ser Asp Gly Asp Phe Ser Glu Met
65                  70                  75                  80 aca ttt agc agt gaa ttg gaa gat gca aga caa att tta aag ttt gtg     288
Thr Phe Ser Ser Glu Leu Glu Asp Ala Arg Gln Ile Leu Lys Phe Val
                 85                  90                  95 aaa gag caa cct acg act gac cct gag aga ata gga cta ctt ggt ttg     336
Lys Glu Gln Pro Thr Thr Asp Pro Glu Arg Ile Gly Leu Leu Gly Leu
                100                 105                 110 agt atg gga gga gct att gca ggg att gta gca agg gaa tat aaa gat     384
Ser Met Gly Gly Ala Ile Ala Gly Ile Val Ala Arg Glu Tyr Lys Asp
            115                 120                 125 gaa ata aag gcg ttg gtg cta tgg gct cca gct ttt aat atg cct gag     432
Glu Ile Lys Ala Leu Val Leu Trp Ala Pro Ala Phe Asn Met Pro Glu
        130                 135                 140 ctt ata atg aac gaa agt gta aag caa tac gga gct att atg gaa caa     480
Leu Ile Met Asn Glu Ser Val Lys Gln Tyr Gly Ala Ile Met Glu Gln
145                 150                 155                 160 ttg ggc ttt gta gac ata gga gga cat aaa ctg agt aaa gat ttt gtt     528
Leu Gly Phe Val Asp Ile Gly Gly His Lys Leu Ser Lys Asp Phe Val
                165                 170                 175 gag gat att tca aaa tta aat ata ttt gag ctg tca aaa gga tac gat     576
Glu Asp Ile Ser Lys Leu Asn Ile Phe Glu Leu Ser Lys Gly Tyr Asp
                180                 185                 190 aaa aaa gtg ctt ata gtt cat ggg aca aat gat gaa gcg gtt gaa tat     624
Lys Lys Val Leu Ile Val His Gly Thr Asn Asp Glu Ala Val Glu Tyr
            195                 200                 205 aaa gtt tct gat aga atc tta aaa gag gtt tat ggg gat aac gct aca     672
Lys Val Ser Asp Arg Ile Leu Lys Glu Val Tyr Gly Asp Asn Ala Thr
        210                 215                 220 aga gtg aca atc gaa aat gca gac cat act ttt aag agt tta gaa tgg     720
Arg Val Thr Ile Glu Asn Ala Asp His Thr Phe Lys Ser Leu Glu Trp
225                 230                 235                 240 gag aaa aag gcg att gag gag tca gta gag ttt ttc aaa aag gaa ttg     768
Glu Lys Lys Ala Ile Glu Glu Ser Val Glu Phe Phe Lys Lys Glu Leu
                245                 250                 255 tta aag gga tag                                                     780
Leu Lys Gly
```

<210> SEQ ID NO 2
<211> LENGTH: 259
<212> TYPE: PRT
<213> ORGANISM: Thermoanaerobacter thermohydrosulfuricus

<400> SEQUENCE: 2

```
Met Gln Lys Ala Val Glu Ile Thr Tyr Asn Gly Lys Thr Leu Arg Gly
1               5                   10                  15

Met Met His Leu Pro Asp Asp Val Lys Gly Lys Val Pro Met Val Ile
            20                  25                  30

Met Phe His Gly Phe Thr Gly Asn Lys Val Glu Ser His Phe Ile Phe
        35                  40                  45
```

```
Val Lys Met Ser Arg Ala Leu Glu Lys Val Gly Ile Gly Ser Val Arg
        50                  55                  60

Phe Asp Phe Tyr Gly Ser Gly Glu Ser Asp Gly Asp Phe Ser Glu Met
 65                  70                  75                  80

Thr Phe Ser Ser Glu Leu Glu Asp Ala Arg Gln Ile Leu Lys Phe Val
                 85                  90                  95

Lys Glu Gln Pro Thr Thr Asp Pro Glu Arg Ile Gly Leu Leu Gly Leu
                100                 105                 110

Ser Met Gly Gly Ala Ile Ala Gly Ile Val Ala Arg Glu Tyr Lys Asp
            115                 120                 125

Glu Ile Lys Ala Leu Val Leu Trp Ala Pro Ala Phe Asn Met Pro Glu
        130                 135                 140

Leu Ile Met Asn Glu Ser Val Lys Gln Tyr Gly Ala Ile Met Glu Gln
145                 150                 155                 160

Leu Gly Phe Val Asp Ile Gly Gly His Lys Leu Ser Lys Asp Phe Val
                165                 170                 175

Glu Asp Ile Ser Lys Leu Asn Ile Phe Glu Leu Ser Lys Gly Tyr Asp
            180                 185                 190

Lys Lys Val Leu Ile Val His Gly Thr Asn Asp Glu Ala Val Glu Tyr
        195                 200                 205

Lys Val Ser Asp Arg Ile Leu Lys Glu Val Tyr Gly Asp Asn Ala Thr
    210                 215                 220

Arg Val Thr Ile Glu Asn Ala Asp His Thr Phe Lys Ser Leu Glu Trp
225                 230                 235                 240

Glu Lys Lys Ala Ile Glu Glu Ser Val Glu Phe Phe Lys Lys Glu Leu
                245                 250                 255

Leu Lys Gly

<210> SEQ ID NO 3
<211> LENGTH: 777
<212> TYPE: DNA
<213> ORGANISM: Thermoanaerobacter tencongensis
<220> FEATURE:
<221> NAME/KEY: CDS
<222> LOCATION: (1)..(774)

<400> SEQUENCE: 3 gtg cag aag gct gta gag ttt aca tat aat agg aaa acc tta agg ggg     48
Val Gln Lys Ala Val Glu Phe Thr Tyr Asn Arg Lys Thr Leu Arg Gly
 1               5                  10                  15 atg ttg cat ctt cct gaa gga gta tct gaa aag gtt cct atg gta gtt     96
Met Leu His Leu Pro Glu Gly Val Ser Glu Lys Val Pro Met Val Val
                20                  25                  30 atg ttt cac ggt ttt aca gga aat aaa gta gag tcc cat ttt att ttt    144
Met Phe His Gly Phe Thr Gly Asn Lys Val Glu Ser His Phe Ile Phe
            35                  40                  45 gtt aag atg tca aga gct tta gaa aaa gtg gga ata gga agt gtg agg    192
Val Lys Met Ser Arg Ala Leu Glu Lys Val Gly Ile Gly Ser Val Arg
        50                  55                  60 ttt gac ttt tac ggt tca ggc gaa agc gac gga gat ttt agt gaa atg    240
Phe Asp Phe Tyr Gly Ser Gly Glu Ser Asp Gly Asp Phe Ser Glu Met
 65                  70                  75                  80 acc ttt agc ggt gaa tta gag gat gca cga cag att tta gat ttc gtt    288
Thr Phe Ser Gly Glu Leu Glu Asp Ala Arg Gln Ile Leu Asp Phe Val
                 85                  90                  95 aaa agg cag ccg act acg gat gta gaa aga ata ggt ctt ttg gga ctc    336
Lys Arg Gln Pro Thr Thr Asp Val Glu Arg Ile Gly Leu Leu Gly Leu
                100                 105                 110
```

```
                                                          -continued
agc atg gga gga gct ata gca gga ata ata gca aga gaa aga aaa gag        384
Ser Met Gly Gly Ala Ile Ala Gly Ile Ile Ala Arg Glu Arg Lys Glu
        115                 120                 125 gat gtg aaa gcc tta gtt tta tgg gct ccc gct ttt aat atg ccg gaa        432
Asp Val Lys Ala Leu Val Leu Trp Ala Pro Ala Phe Asn Met Pro Glu
130                 135                 140 ctc ata atg gga gaa gga gct aga cag tat ggg gca ata atg gaa agc        480
Leu Ile Met Gly Glu Gly Ala Arg Gln Tyr Gly Ala Ile Met Glu Ser
145                 150                 155                 160 ttg ggc tat gta gat ata ggg gga cta aaa ctt gac aga gct ttt gtg        528
Leu Gly Tyr Val Asp Ile Gly Gly Leu Lys Leu Asp Arg Ala Phe Val
                165                 170                 175 gag gat ata gcg aag ttt aat att ttt gag ctg tca aga ggt tat gag        576
Glu Asp Ile Ala Lys Phe Asn Ile Phe Glu Leu Ser Arg Gly Tyr Glu
            180                 185                 190 ggg aaa gtg ctc ata gtc cac ggt act aac gat gaa gcc gtt gag tac        624
Gly Lys Val Leu Ile Val His Gly Thr Asn Asp Glu Ala Val Glu Tyr
        195                 200                 205 agg atc tct gat aga ata ctt caa gaa gta tat ggg gat aat gct ttc        672
Arg Ile Ser Asp Arg Ile Leu Gln Glu Val Tyr Gly Asp Asn Ala Phe
    210                 215                 220 cgc gta act ata gaa gga gcg gac cat act ttt aaa aac ctt gaa tgg        720
Arg Val Thr Ile Glu Gly Ala Asp His Thr Phe Lys Asn Leu Glu Trp
225                 230                 235                 240 gaa aga aaa gcg ata gaa gaa tct gtg aag ttc ttt gaa aga gaa tta        768
Glu Arg Lys Ala Ile Glu Glu Ser Val Lys Phe Phe Glu Arg Glu Leu
                245                 250                 255 aag gga tag                                                            777
Lys Gly <210> SEQ ID NO 4
<211> LENGTH: 258
<212> TYPE: PRT
<213> ORGANISM: Thermoanaerobacter tencongensis

<400> SEQUENCE: 4

Val Gln Lys Ala Val Glu Phe Thr Tyr Asn Arg Lys Thr Leu Arg Gly
 1               5                  10                  15

Met Leu His Leu Pro Glu Gly Val Ser Glu Lys Val Pro Met Val Val
            20                  25                  30

Met Phe His Gly Phe Thr Gly Asn Lys Val Glu Ser His Phe Ile Phe
        35                  40                  45

Val Lys Met Ser Arg Ala Leu Glu Lys Val Gly Ile Gly Ser Val Arg
    50                  55                  60

Phe Asp Phe Tyr Gly Ser Gly Glu Ser Asp Gly Asp Phe Ser Glu Met
65                  70                  75                  80

Thr Phe Ser Gly Glu Leu Glu Asp Ala Arg Gln Ile Leu Asp Phe Val
                85                  90                  95

Lys Arg Gln Pro Thr Thr Asp Val Glu Arg Ile Gly Leu Leu Gly Leu
            100                 105                 110

Ser Met Gly Gly Ala Ile Ala Gly Ile Ile Ala Arg Glu Arg Lys Glu
        115                 120                 125

Asp Val Lys Ala Leu Val Leu Trp Ala Pro Ala Phe Asn Met Pro Glu
    130                 135                 140

Leu Ile Met Gly Glu Gly Ala Arg Gln Tyr Gly Ala Ile Met Glu Ser
145                 150                 155                 160

Leu Gly Tyr Val Asp Ile Gly Gly Leu Lys Leu Asp Arg Ala Phe Val
                165                 170                 175
```

```
Glu Asp Ile Ala Lys Phe Asn Ile Phe Glu Leu Ser Arg Gly Tyr Glu
            180                 185                 190

Gly Lys Val Leu Ile Val His Gly Thr Asn Asp Glu Ala Val Glu Tyr
        195                 200                 205

Arg Ile Ser Asp Arg Ile Leu Gln Glu Val Tyr Gly Asp Asn Ala Phe
    210                 215                 220

Arg Val Thr Ile Glu Gly Ala Asp His Thr Phe Lys Asn Leu Glu Trp
225                 230                 235                 240

Glu Arg Lys Ala Ile Glu Gly Ser Val Lys Phe Phe Glu Arg Glu Leu
                245                 250                 255

Lys Gly

<210> SEQ ID NO 5
<211> LENGTH: 23
<212> TYPE: DNA
<213> ORGANISM: Thermoanaerobacter thermohydrosulfuricus

<400> SEQUENCE: 5
atgcaaaagg ctgttgaaat tac                                        23

<210> SEQ ID NO 6
<211> LENGTH: 25
<212> TYPE: DNA
<213> ORGANISM: Thermoanaerobacter thermohydrosulfuricus

<400> SEQUENCE: 6
ttatcccttt aacaattcct ttttg                                      25

<210> SEQ ID NO 7
<211> LENGTH: 23
<212> TYPE: DNA
<213> ORGANISM: Caldanaerobacter subterraneus subsp. tengcongensis

<400> SEQUENCE: 7
atgcagaagg ctgtagagtt tac                                        23

<210> SEQ ID NO 8
<211> LENGTH: 25
<212> TYPE: DNA
<213> ORGANISM: Caldanaerobacter subterraneus subsp. tengcongensis

<400> SEQUENCE: 8
ttatcccttt aattctcttt caaag                                      25

<210> SEQ ID NO 9
<211> LENGTH: 23
<212> TYPE: DNA
<213> ORGANISM: Thermoanaerobacter thermohydrosulfuricus

<400> SEQUENCE: 9 cttaagggggg atgttgcatc ttc                                       23

<210> SEQ ID NO 10
<211> LENGTH: 22
<212> TYPE: DNA
<213> ORGANISM: Thermoanaerobacter thermohydrosulfuricus

<400> SEQUENCE: 10
attaaggggg gtactgcatc tg                                         22

<210> SEQ ID NO 11
<211> LENGTH: 25
```

-continued

```
<212> TYPE: DNA
<213> ORGANISM: Thermoanaerobacter thermohydrosulfuricus

<400> SEQUENCE: 11
catgggttta ccgaaataa agtgg                                          25

<210> SEQ ID NO 12
<211> LENGTH: 20
<212> TYPE: DNA
<213> ORGANISM: Thermoanaerobacter thermohydrosulfuricus

<400> SEQUENCE: 12
ttcaggcgaa agcgacggag                                               20

<210> SEQ ID NO 13
<211> LENGTH: 26
<212> TYPE: DNA
<213> ORGANISM: Thermoanaerobacter thermohydrosulfuricus

<400> SEQUENCE: 13
ggaacaggtg aaagtgatgg agaatt                                        26

<210> SEQ ID NO 14
<211> LENGTH: 23
<212> TYPE: DNA
<213> ORGANISM: Thermoanaerobacter thermohydrosulfuricus

<400> SEQUENCE: 14
gcggtgaaag tgatggagac ttt                                           23

<210> SEQ ID NO 15
<211> LENGTH: 20
<212> TYPE: DNA
<213> ORGANISM: Thermoanaerobacter thermohydrosulfuricus

<400> SEQUENCE: 15
tccgtcgctt tcgcctgaac                                               20

<210> SEQ ID NO 16
<211> LENGTH: 27
<212> TYPE: DNA
<213> ORGANISM: Thermoanaerobacter thermohydrosulfuricus

<400> SEQUENCE: 16
aaattctcca tcactttcac ctgttcc                                       27

<210> SEQ ID NO 17
<211> LENGTH: 21
<212> TYPE: DNA
<213> ORGANISM: Thermoanaerobacter thermohydrosulfuricus

<400> SEQUENCE: 17
tctccatcac tttcaccgct g                                             21

<210> SEQ ID NO 18
<211> LENGTH: 21
<212> TYPE: DNA
<213> ORGANISM: Thermoanaerobacter thermohydrosulfuricus

<400> SEQUENCE: 18
tcctcccatg ctgagtccca a                                             21

<210> SEQ ID NO 19
<211> LENGTH: 21
```

```
<212> TYPE: DNA
<213> ORGANISM: Thermoanaerobacter thermohydrosulfuricus

<400> SEQUENCE: 19
tcctcccatg ctgaagccaa g                                              21

<210> SEQ ID NO 20
<211> LENGTH: 24
<212> TYPE: DNA
<213> ORGANISM: Thermoanaerobacter thermohydrosulfuricus

<400> SEQUENCE: 20
ttttgtatgg tccgctcctt ctat                                           24

<210> SEQ ID NO 21
<211> LENGTH: 142
<212> TYPE: DNA
<213> ORGANISM: Thermoanaerobacter tencongensis

<400> SEQUENCE: 21
tgcggtgaaa gtgatggaga ctttagtgaa atgacattta gcagtgaatt ggaagatgca    60
agacaaattt taaagtttgt gaaagagcaa cctacgactg accctgagag aataggacta   120
cttgggactc agcatgggag ga                                            142

<210> SEQ ID NO 22
<211> LENGTH: 141
<212> TYPE: DNA
<213> ORGANISM: Thermoanaerobacter tencongensis

<400> SEQUENCE: 22
tgcggtgaaa gtgatggaga ctttagtgaa atgacattta gcagtgaatt ggaagatgca    60
agacaaattt taaagtttgt gaaagagcaa cctacgactg accctgagag aataggacta   120
cttggcttca gcatgggagg a                                             141

<210> SEQ ID NO 23
<211> LENGTH: 27
<212> TYPE: DNA
<213> ORGANISM: Thermoanaerobacter thermohydrosulfuricus

<400> SEQUENCE: 23
gacatttagc agtgaattgg aagatgc                                        27

<210> SEQ ID NO 24
<211> LENGTH: 25
<212> TYPE: DNA
<213> ORGANISM: Thermoanaerobacter thermohydrosulfuricus

<400> SEQUENCE: 24
tttgtgaaag agcctacgac tgacc                                          25

<210> SEQ ID NO 25
<211> LENGTH: 26
<212> TYPE: DNA
<213> ORGANISM: Thermoanaerobacter thermohydrosulfuricus

<400> SEQUENCE: 25
gcactttacc cttaacatca tcaggc                                         26

<210> SEQ ID NO 26
<211> LENGTH: 27
<212> TYPE: DNA
<213> ORGANISM: Thermoanaerobacter thermohydrosulfuricus
```

```
<400> SEQUENCE: 26
gactctactt tattgcctgt aaaaccg                                                 27

<210> SEQ ID NO 27
<211> LENGTH: 46
<212> TYPE: DNA
<213> ORGANISM: Thermoanaerobacter thermohydrosulfuricus

<400> SEQUENCE: 27
tgaaaaaaag gagaggataa agaatgcaaa aggctgttga aattac                            46

<210> SEQ ID NO 28
<211> LENGTH: 46
<212> TYPE: DNA
<213> ORGANISM: Thermoanaerobacter thermohydrosulfuricus

<400> SEQUENCE: 28
ggagcggatt gaacatgcga ttatcccttt aacaattcct ttttga                            46

<210> SEQ ID NO 29
<211> LENGTH: 21
<212> TYPE: DNA
<213> ORGANISM: Thermoanaerobacter thermohydrosulfuricus

<400> SEQUENCE: 29
gagtatcgcc agtaaggggc g                                                       21

<210> SEQ ID NO 30
<211> LENGTH: 29
<212> TYPE: DNA
<213> ORGANISM: Thermoanaerobacter thermohydrosulfuricus

<400> SEQUENCE: 30
tctttatcct ctccttttt tcagagctc                                                29

<210> SEQ ID NO 31
<211> LENGTH: 23
<212> TYPE: DNA
<213> ORGANISM: Thermoanaerobacter thermohydrosulfuricus

<400> SEQUENCE: 31
gcagccctaa aatcgcataa agc                                                     23

<210> SEQ ID NO 32
<211> LENGTH: 23
<212> TYPE: DNA
<213> ORGANISM: Thermoanaerobacter thermohydrosulfuricus

<400> SEQUENCE: 32
taatcgcatg ttcaatccgc tcc                                                     23
```